United States Patent
Fan

(10) Patent No.: US 10,314,467 B2
(45) Date of Patent: Jun. 11, 2019

(54) ENDOSCOPE

(71) Applicant: SG ENDOSCOPY PTE. LTD., Singapore (SG)

(72) Inventor: Jin Mei Fan, Singapore (SG)

(73) Assignee: SG ENDOSCOPY PTE. LTD., Singapore (SG)

(*) Notice: Subject to any disclaimer, the term of this patent is extended or adjusted under 35 U.S.C. 154(b) by 327 days.

(21) Appl. No.: 14/760,795

(22) PCT Filed: Jan. 14, 2014

(86) PCT No.: PCT/SG2014/000011
§ 371 (c)(1),
(2) Date: Jul. 14, 2015

(87) PCT Pub. No.: WO2014/109715
PCT Pub. Date: Jul. 17, 2014

(65) Prior Publication Data
US 2015/0374214 A1    Dec. 31, 2015

(30) Foreign Application Priority Data
Jan. 14, 2013  (SG) .............................. 201300282-9

(51) Int. Cl.
*A61B 1/00* (2006.01)
*A61B 1/018* (2006.01)
*G02B 23/24* (2006.01)

(52) U.S. Cl.
CPC .......... *A61B 1/018* (2013.01); *A61B 1/00066* (2013.01); *A61B 1/00128* (2013.01); *A61B 1/00137* (2013.01); *G02B 23/2476* (2013.01)

(58) Field of Classification Search
CPC ............ A61B 1/00105; A61B 1/00066; A61B 1/00119
(Continued)

(56) References Cited

U.S. PATENT DOCUMENTS

| 2009/0221873 A1* | 9/2009 | McGrath ............ A61B 1/00128 600/153 |
| 2010/0280311 A1* | 11/2010 | McGrath ............ A61B 1/00105 600/104 |

FOREIGN PATENT DOCUMENTS

| JP | 06-007288 A | 1/1994 |
| JP | 2005-185636 A | 7/2005 |

(Continued)

OTHER PUBLICATIONS

International Search Report dated Mar. 4, 2014, issued for PCT/SG2014/000011.

*Primary Examiner* — Alexandra L Newton
*Assistant Examiner* — Rynae Boler
(74) *Attorney, Agent, or Firm* — Locke Lord LLP

(57) ABSTRACT

An endoscope includes a flexible tube having a curved part at a tip and an endoscope main body part operating a curving operation on the curved part for work, the endoscope having a treatment tool insertion part for inserting a treatment tool projecting from the endoscope main body part and for use in a treatment of a subject into a treatment tool insertion tube arranged in the curved part along an axial direction, wherein the treatment tool insertion part includes an attachment and removal part having an insertion tube and a body, the insertion tube having one end inserted in the endoscope main body part to be arranged to communicate to the treatment tool insertion tube and another end placed outside the endoscope main body part, and the body holding and fixing the insertion tube to the endoscope main body part.

6 Claims, 6 Drawing Sheets

(58) Field of Classification Search
USPC .................................. 600/104, 106, 153
See application file for complete search history.

(56) References Cited

FOREIGN PATENT DOCUMENTS

| | | |
|---|---|---|
| JP | 2011-010672 A | 1/2011 |
| JP | 2011-062299 A | 3/2011 |

* cited by examiner

ENDOSCOPE

CROSS REFERENCE TO RELATED APPLICATIONS

This applications is related to three co-pending applications: "ENDOSCOPE OPERATING APPARATUS" filed even date herewith in the name Jin Mei Fan as a national phase entry of PCT/SG2014/000010; and "BENDING OPERATION APPARATUS FOR ENDOSCOPE AND ENDOSCOPE" filed even date herewith in the name Jin Mei Fan as a national phase entry of PCT/SG2014/000012; which applications are assigned to the assignee of the present application and all three incorporated by reference herein.

TECHNICAL FIELD

The present invention relates to an endoscope and, in particular, to an improvement of a treatment tool insertion part provided to the endoscope.

BACKGROUND ART

Conventionally, endoscopes have been used in the medical and other fields for the purpose of examinations and treatments. An endoscope 200 of this type includes, as depicted in FIG. 6, a main body part 201 and a flexible tube 203 to be joined to the main body part 201 and inserted inside the body of a person to be operated and having a curved part 202 at the tip. The main body part 201 is provided with an operating part 204 capable of curving the curved part 202 provided at the tip of the flexible tube 203 as appropriate.

Inside the flexible tube 203, an operation wire (not shown) is arranged, having a tip fixed to the curved part 202 for curving the curved part 202 by pulling. By driving and pulling this operation wire by appropriate means, the curved part 202 is curved in upper, lower, left, and right directions for examination, treatment, and others. The main body part 201 is provided with an operating part 204. In the case of a manual operation by an operator, a wire pulling operation is generally performed by a rotary dial 205.

Inside the flexible tube 203, a forceps channel 206 through which any of various treatment tools is inserted is provided. When a region required to be examined is found in an internal organ at the time of examination, for example, a metal ring called a snare is hooked in the region required to be examination and, for example, a high-frequency current is caused to flow through to cut the region (endoscopic mucosal resection) or a large lesion is cut out by a dedicated treatment tool (endoscopic submucosal dissection), thereby checking the state of a tissue with a microscope.

Therefore, in the main body part 201 of the endoscope, a treatment tool insertion part 207 is provided so as to allow various treatment tools to be inserted from outside through the forceps channel 206 to project from the tip of the curved part 202 to the inside of the internal organ.

In this case, since a portion required to be examined is extracted or blood is suctioned by various treatment tools through the treatment tool insertion part 207, the inside of the treatment tool insertion part is required to be clean and, when used in an examination, is always subjected to sterilization and disinfection by means of sterilization with EOG (ethylene oxide gas), sterilization with gamma rays, sterilization by boiled water, and others. Also, if frequently used with a treatment tool or the like inserted thereinto, the treatment tool insertion part may be broken, possibly leading to replacement as required. Therefore, the treatment tool insertion part is desired to allow easy sterilization and disinfection and to be easily removed.

However, the treatment tool insertion part 207 itself of the conventional endoscope is not configured to be removable from the main body part 201 (Patent Document 1).

Moreover, it has been conventionally suggested that a treatment tool insertion part is configured in an operating part of an endoscope with a base end part projecting outward and integrally provided and a tip part removably jointed to the base end part (Patent Document 2).

However, in the technology described in Patent Document 2, while the tip part can be removed, the base end part forming the treatment tool insertion part is integrally provided to an operating part of the endoscope, and therefore an inconvenience still exists such that cleaning and disinfection and sterilization of a treatment tool insertion tube inside may not be able to be easily performed at the time of clearing and disinfection and sterilization Moreover, since the treatment tool insertion part has various insertion tools inserted therein and removed therefrom, the treatment tool insertion part may be broken and be required to be replaced. However, the conventional treatment tool insertion part is configured of the base end part and the tip part, has a complex structure, and has a possibility of being easily broken, and even in the case of component replacement, there is a possibility of increasing component cost.

[Patent Document 1] Japanese Utility Model Publication No. 1-11201
[Patent Document 2] Japanese Unexamined Patent Application Publication No. 2005-185636

DISCLOSURE OF THE INVENTION

Problems to be Solved by the Invention

The present invention is to solve these conventional inconveniences, and has a problem of providing an endoscope having a treatment tool insertion part capable of allowing easy cleaning and disinfection and sterilization and also decreasing the number of components to reduce manufacturing cost.

Means for Solving the Problem

According to the first aspect to the present invention, an endoscope includes a flexible tube having a curved part at a tip and an endoscope main body part operating a curving operation on the curved part for work, the endoscope having a treatment tool insertion part for inserting a treatment tool projecting from the endoscope main body part and for use in a treatment of a subject into a treatment tool insertion tube arranged in the curved part along an axial direction, wherein the treatment tool insertion part includes an attachment and removal part having an insertion tube and a body, the insertion tube having one end inserted in the endoscope main body part to be arranged to communicate to the treatment tool insertion tube and another end placed outside the endoscope main body part, and the body holding and fixing the insertion tube to the endoscope main body part and the treatment tool insertion part also includes a support part provided on the endoscope main body part and having an insertion part and a tube path part, the insertion part through which the insertion tube is inserted and removed, and the tube path part communicating to the treatment tool insertion tube.

According to the second aspect to the present invention, the support part is provided with an engaging member arranged to project from an outer side surface part of the endoscope main body part, and an engaging part that can be engaged with the engaging member is formed on the body.

According to the third aspect to the present invention, the engaging member is formed of a leaf spring member formed in an approximately U shape in a longitudinal sectional view, has paired side piece parts facing each other and a fixing piece part continuously provided between the paired side piece parts, the paired side piece parts each has a swelling part formed thereon, the swelling part formed to swell inward, the body has an insertion hollow part of the engaging member formed thereon, and the tube part is provided with an engaging part having a recessed part where the swelling part is inserted and fixed.

According to the fourth aspect to the present invention, the support part configures the endoscope main body part and is fixed inside the tube part having an opening on an upper part, with an upper surface part of the support part being provided so as to be exposed from the opening toward outside.

According to the fifth aspect to the present invention, the insertion tube is arranged along the axial direction of the endoscope main boy part and diagonally with respect to the axial direction, the body is formed of a covering part covering the insertion tube and a fixing part continuously provided to the covering part and capable of being fixed to the mount part.

According to the sixth aspect to the present invention, the mount part is configured as a projection part having an insertion hole, the mount part is provided with an opening that can communicate to the insertion hole and, when the insertion hole and the opening communicate to each other, fixing is made with an insertion member capable of being inserted.

Effect of the Invention

According to the first aspect to the present invention, the treatment tool insertion part includes an attachment and removal part having an insertion tube and a body, the insertion tube having one end inserted in the endoscope main body part to be arranged to communicate to the treatment tool insertion tube and another end placed outside the endoscope main body part, and the body holding and fixing the insertion tube to the endoscope main body part; and a support part provided on the endoscope main body part and having an insertion part and a tube path part, the insertion part through which the insertion tube is inserted and removed, and the tube path part communicating to the treatment tool insertion tube. Thus, with the attachment and removal part being removed, cleaning can be easily performed. Also, disinfection and sterilization can be performed with various disinfection and sterilization schemes. Therefore, the treatment tool insertion part can be kept always clean.

Also, according to the first aspect to the present invention, less components are included, and the number of components can be decreased, and therefore the manufacturing cost can be reduced. As a result, it is possible to provide an endoscope having a treatment tool insertion part that can be easily replaced without trouble if broken with a lapse of time after use and is excellent in maintenability.

According to the second aspect to the present invention, the support part is provided with an engaging member arranged to project from an outer side surface part of the endoscope main body part, and an engaging part that can be engaged with the engaging member is formed on the body. Thus, it is possible to provide an endoscope having a treatment tool insertion part that can be easily attached and removed.

According to the third aspect to the present invention, the engaging member is formed of a leaf spring member formed in an approximately U shape in a longitudinal sectional view, has paired side piece parts facing each other and a fixing piece part continuously provided between the paired side piece parts, the paired side piece parts each have a swelling part formed thereon, the swelling part formed to swell inward, the body has an insertion hollow part of the engaging member formed thereon, and the tube part is provided with an engaging part having a recessed part where the swelling part is inserted and fixed. When the attachment and removal part is fixed to the support part, with a pressing force produced with the paired side piece parts curved outward, the swelling part is inserted and fixed into the recessed part. This achieves easy and reliable fixing.

Also, in releasing fixing of the attachment and removal part, when the attachment and removal part is extracted, as with the case of fixing, the paired side piece parts are curved outward. Thus, the engagement of the engaging part can be easily released.

According to the fourth aspect to the present invention, the support part configures the endoscope main body part and is fixed inside the tube part having an opening on an upper part, with an upper surface part of the support part being provided so as to be exposed from the opening toward outside. Thus, the number of components can be reduced, and manufacturing cost can be reduced.

According to the fifth aspect to the present invention, the insertion tube is arranged along the axial direction of the endoscope main boy part and diagonally with respect to the axial direction, the body is formed of a covering part covering the insertion tube and a fixing part continuously provided to the covering part and capable of being fixed to the mount part. Thus, an endoscope having a treatment tool insertion part insertion part with the insertion tube easily attachable to and removable from the endoscope main body part can be provided.

According to the sixth aspect to the present invention, the fixing part is configured as a projection part having an insertion hole, the body is provided with an opening that can communicate to the insertion hole and, when the insertion hole and the opening communicate to each other, fixing is made with an insertion member capable of being inserted. Thus, an endoscope allowing an easy and quick work of attaching and removing the treatment tool insertion part can be provided.

MODE FOR CARRYING OUT THE INVENTION

The present invention is described in detail below based on an embodiment depicted in the attached drawings.

Figure 1:
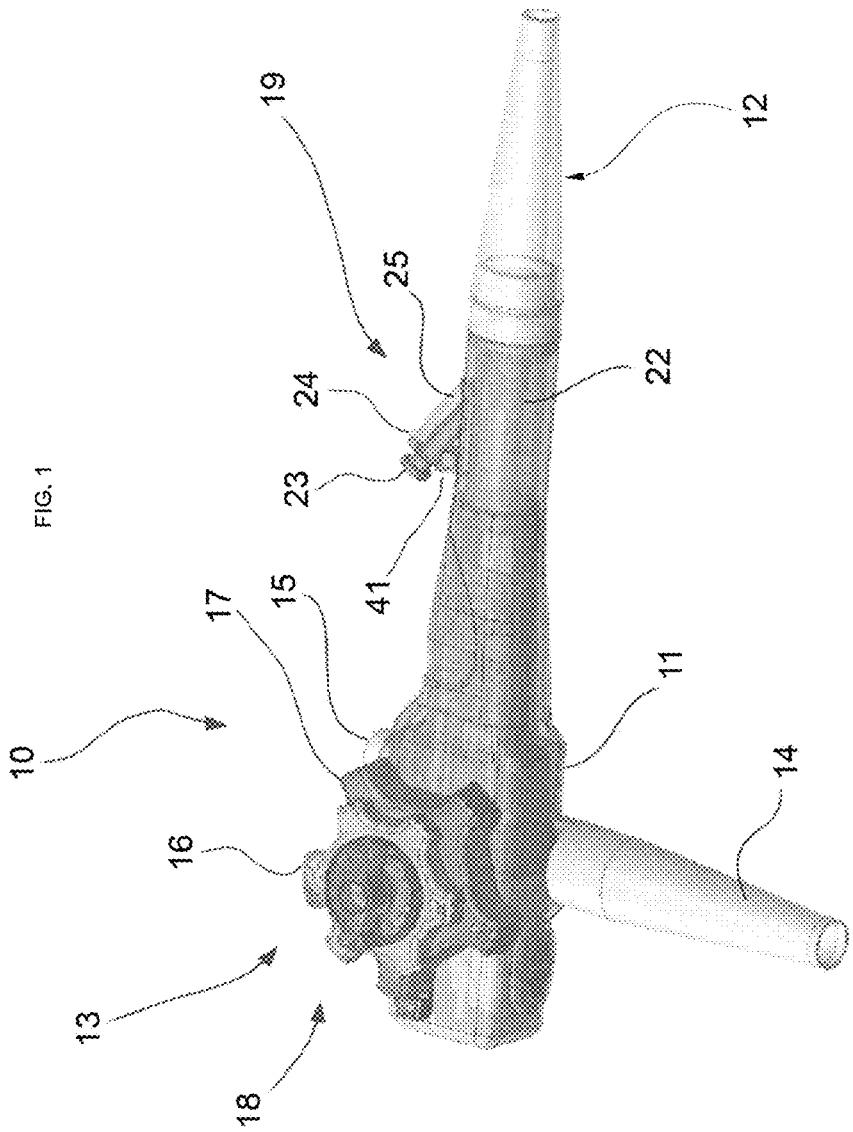
FIG. 1 A perspective view of an endoscope main body part of an endoscope according to one embodiment of the present invention.

FIG. 1 is a perspective view of an endoscope main body part 10 according to an embodiment.

At the tip of the endoscope main body part 10, a joint part 12 having a curved part at the tip and joining to a flexible tube (not shown) is provided, and an endoscope operating device 13 is provided at a rear end. Note that 14 in the drawing denotes a connecting part of a light guide cable and 15 in the drawing denotes an air supply/water supply valve.

In the present embodiment, on a body 11 configuring the endoscope main body part 10, an upper-and-lower-direction rotation operating part 16 and a left-and-right rotation operating part 17 continuously provided above the upper-and-lower-direction rotation operating part 16 are provided, which form an operating part 18.

Between the endoscope operating device 13 and the joint part 12 described above, a treatment tool insertion part 19 is arranged for inserting a treatment tool for use in a treatment of a subject into a treatment tool insertion tube arranged in the flexible tube along an axial direction.

Figure 2:
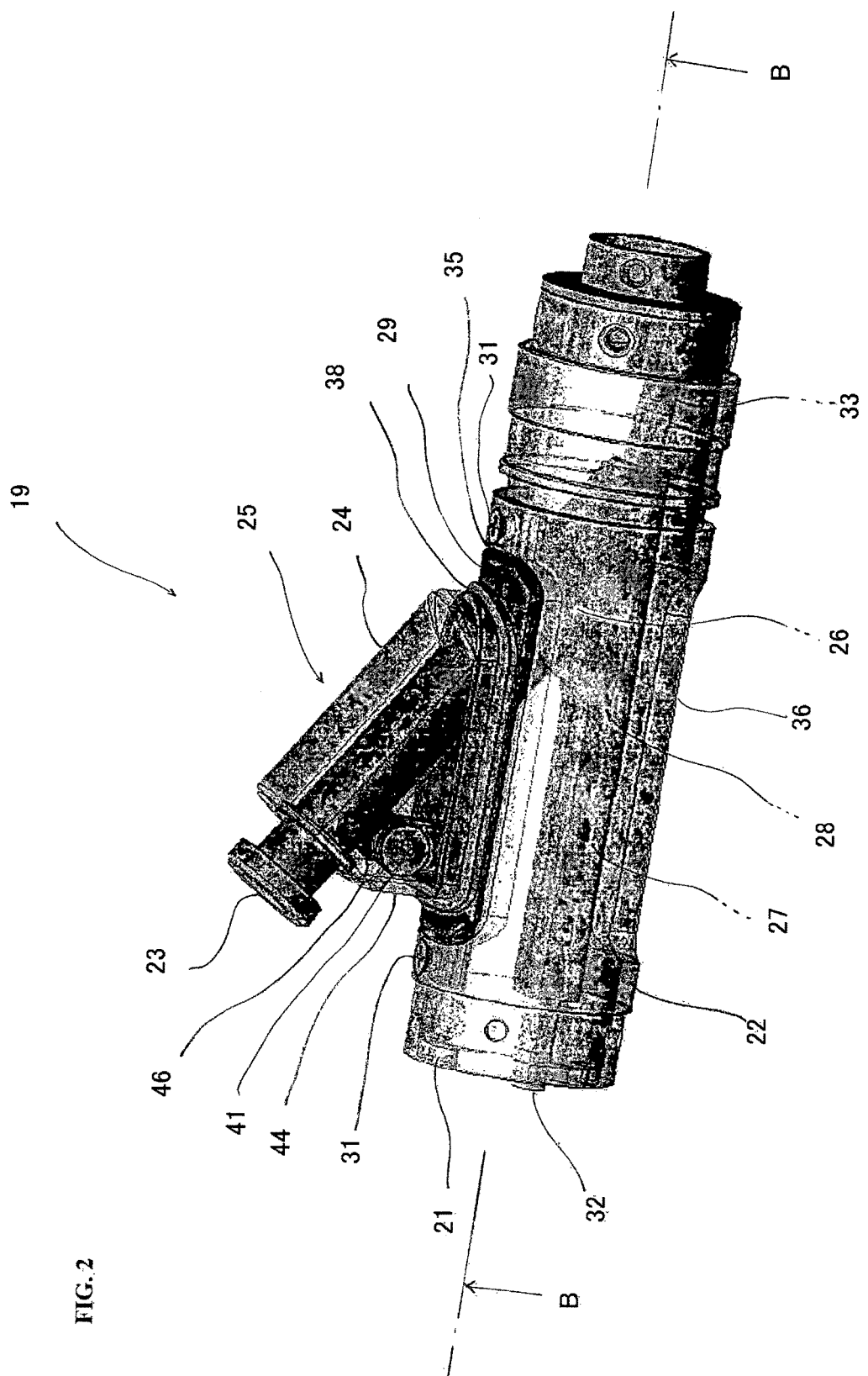
FIG. 2 A perspective view of a treatment tool insertion part for use in the endoscope according to one embodiment of the present invention.

As depicted in FIG. 1 and FIG. 2, the treatment tool insertion part 19 includes a tube part 21 having a cylindrical panel part 22 on its front surface and having openings 35 and 36 provided to be open on its upper and lower surface parts, respectively, each in an approximately rectangular shape in a planar view; an attachment and removal part 25 having an insertion tube 23 and a body 24, the insertion tube 23 arranged on the tube part 21 and having one end inserted in the tube part 21 configuring the endoscope main body part 10 to be arranged to communicate to the treatment tool insertion tube and the other end placed outside the tube part 21 configuring the endoscope main body part 10, and the body 24 holding and fixing the insertion tube 23 to the endoscope main body part 10; and a support part 28 having an insertion part 26 and a tube path part 27, the insertion part 26 in a tube path shape arranged in the tube part 21 configuring the endoscope main body part 10 and through which the insertion tube 23 is inserted and removed, and the tube path part 27 communicating to the treatment tool insertion tube.

Figure 3:
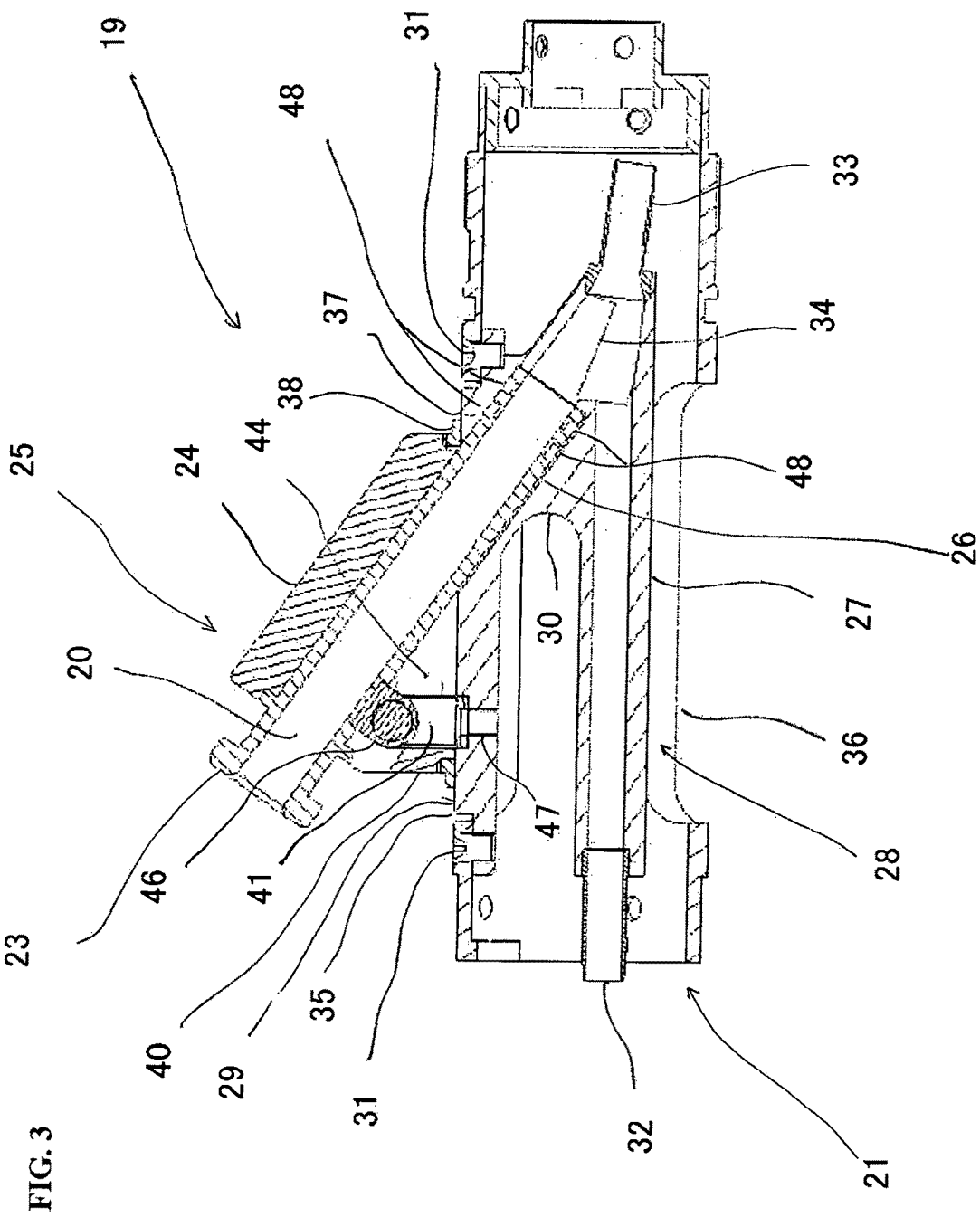
FIG. 3 A longitudinal sectional view along a B-B line of FIG. 2 showing the treatment tool insertion part for use in the endoscope according to one embodiment of the present invention.
Figure 4:
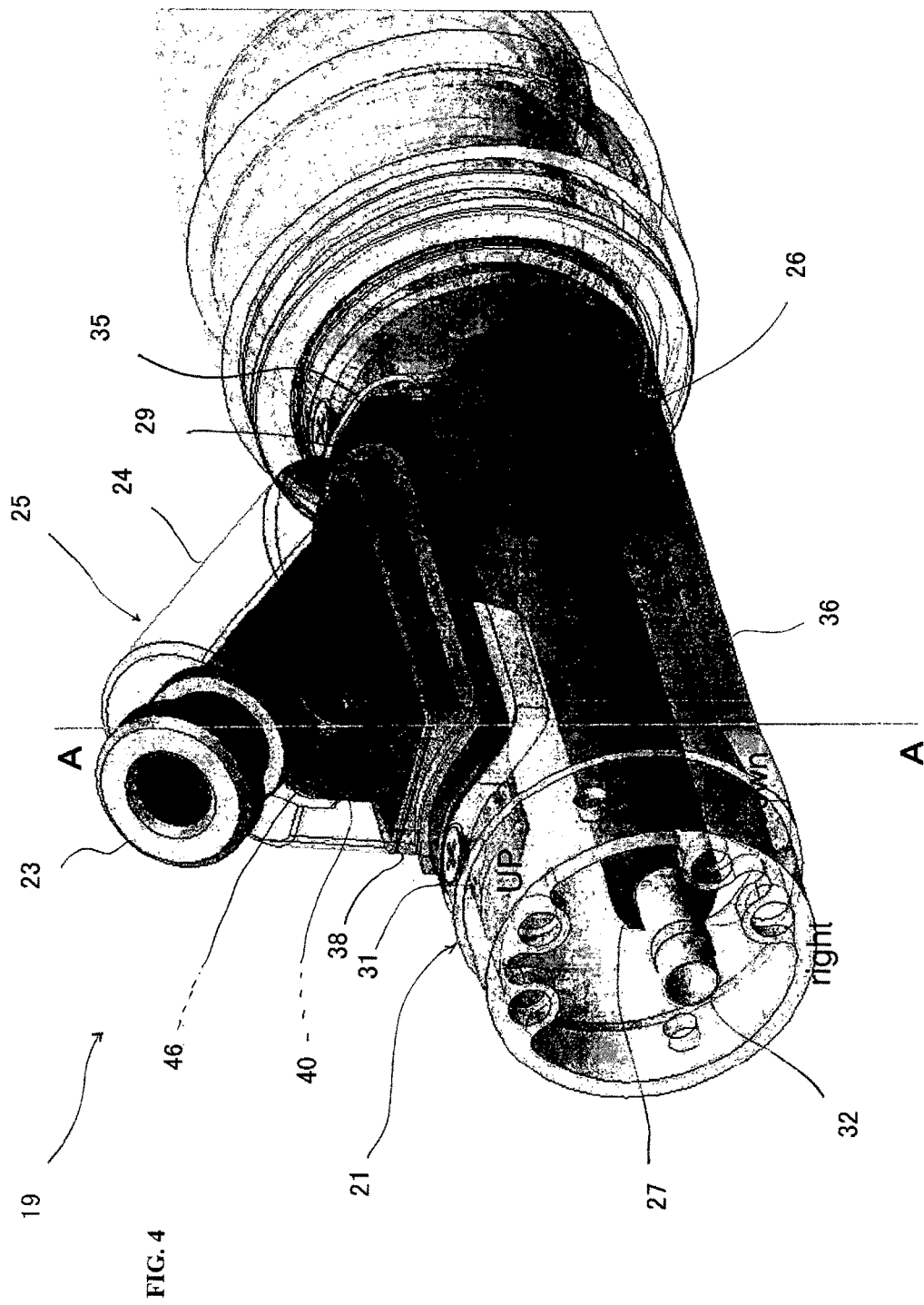
FIG. 4 A perspective view of the treatment tool insertion part for use in the endoscope according to one embodiment of the present invention.
Figure 5:
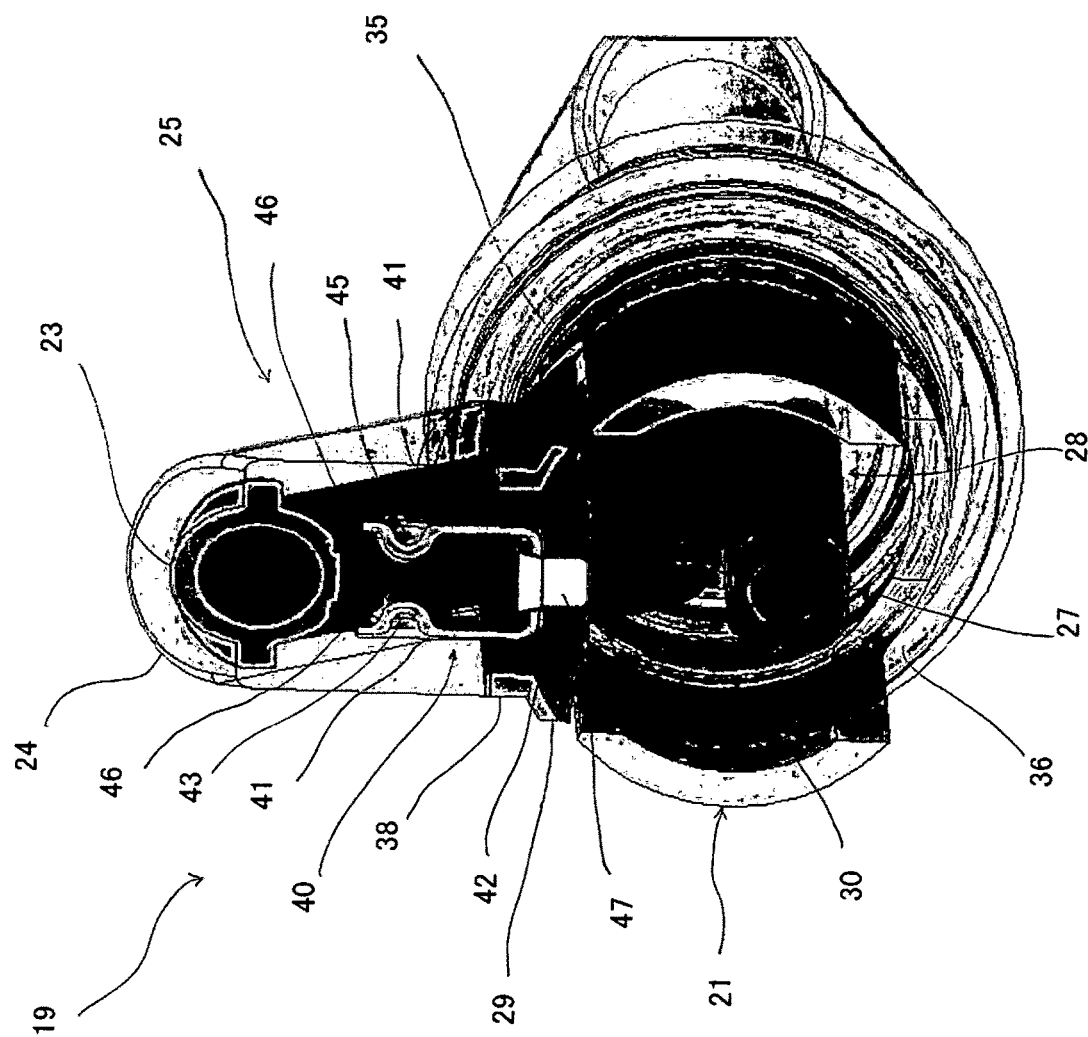
FIG. 5 A sectional view of the treatment tool insertion part for use in the endoscope according to one embodiment of the present invention, and a longitudinal sectional view along an A-A line of FIG. 4.
Figure 6:
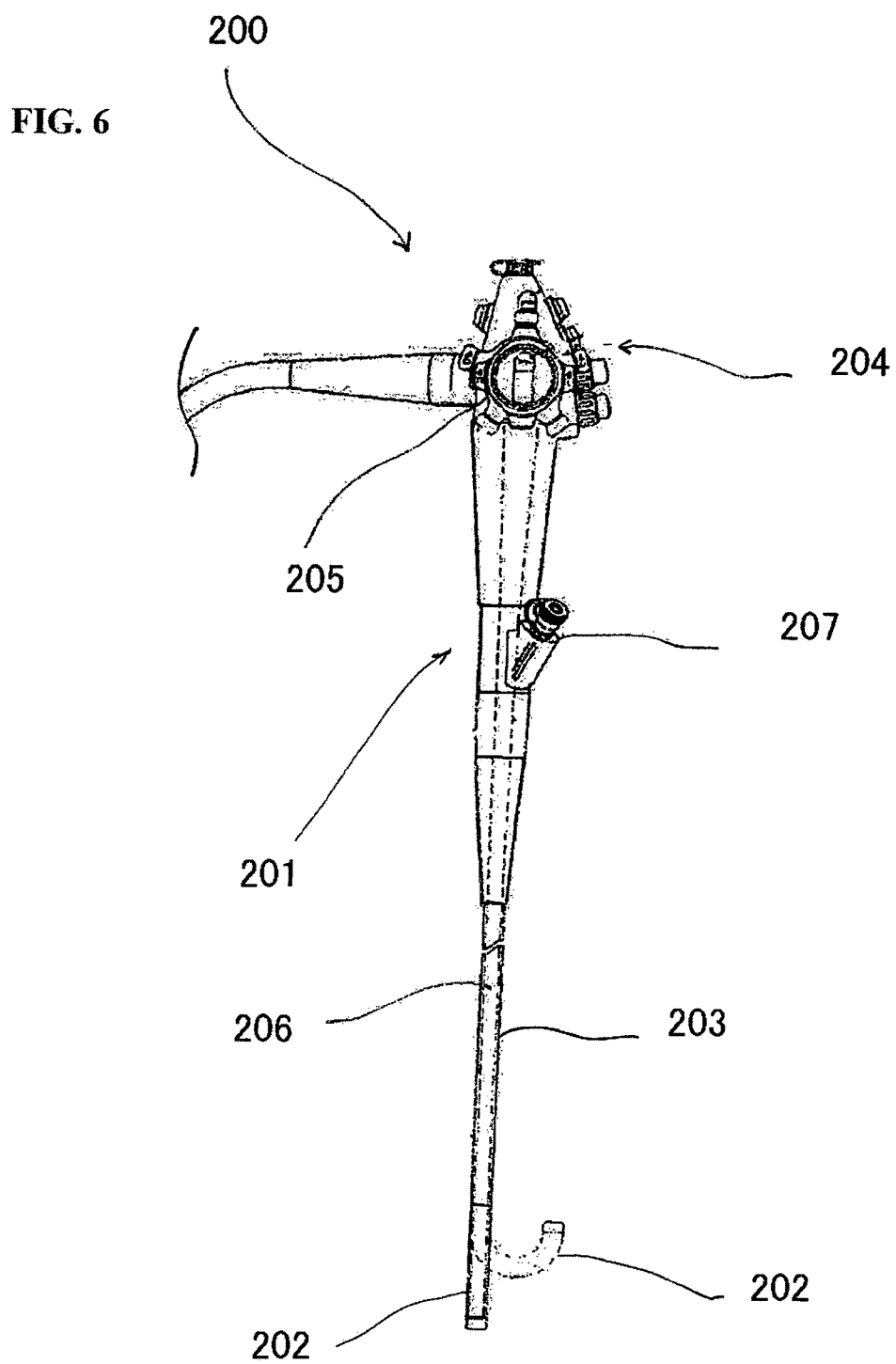
FIG. 6 A plan view generally depicting a conventional endoscope.

As depicted in FIG. 2 and FIG. 3, the support part 28 is formed to be bifurcated, a fixing plate part 29 is formed a predetermined space apart from the tube path part 27 in parallel, and the tube path part 27 and the insertion part 26 are coupled together via a connecting part 30 and fixed to an upper surface part of the tube part 21 with the fixing plate part 29 and fixed inside the tube part 21 with screws 31, 31. A thick part 37 of the fixing plate part 29 is placed so as to be exposed to the upper surface via the opening 35 formed on the upper surface part of the tube part 21, configuring a mount part of the attachment and removal part 25.

The tube path part 27 has a rear end part to which a pipe 32 is joined, is connected to a suction valve with the pipe 32 via a tube made of synthetic resin, and has a tip part to which a pipe 33 is fixed to be connected to the treatment tool insertion tube.

The insertion part 26 is formed of a cylindrical hollow part heading for a direction of the operating part 18 open outward in a diameter direction of the tube part 21. The insertion part 26 has a lower end part where a tapered part 34 in a truncated cone shape is formed, and communicates to the pipe 33 via the tapered part 34.

The insertion tube 23 configuring the attachment and removal part 25 is made of hard rubber, and has an outer diameter formed so as to be slightly smaller than the inner diameter of the insertion part 26. When the attachment and removal part 25 is inserted into the tube part 21, the tip part is arranged to be inserted into the insertion part 26. The tip part of the insertion tube 23 has O rings 48, 48 arranged with a predetermined spacing to ensure hermeticity between the insertion tube 23 and the insertion part 26.

The body 24 is made of hard rubber, is formed in an approximately triangular pyramid shape as a whole as depicted in FIG. 2, and is joined to the insertion tube 23 to cover and fix the entire insertion tube 23.

The thick part 37 has a surface part to which a rubber-made seal member 38 formed in a rectangular frame shape in a planar view is fixed and configured to abut on a back surface of the lower end part of the body 24 of the attachment and removal part 25.

On the surface part of the thick part 37, an engaging member 40 arranged to project from an outer side surface part of the tube part 21 configuring the endoscope main body part 10 is provided. The insertion tube 23 has a lower part to which an engaging part 46 capable of engaging with the engaging member 40 is fixed.

The engaging member 40 is formed of a metal-made leaf spring member formed in an approximately U shape in a longitudinal sectional view, and has paired side piece parts 41, 41 facing each other and a fixing piece part 42 continuously provided between the paired side piece parts 41, 41. On the paired side piece parts 42, 42, swelling parts 43, 43 formed to project inward are formed.

The engaging member 40 is fixed to a fixing plate part 29 of the support part 28 on the fixing piece part 42 with a screw 47.

The body 24 has an insertion hollow part 44 for the engaging member 40 formed therein, and the tube part 21 is provided with an engaging part 46 formed of a projection part and provided with a through hole part 45 where the swelling parts 43, 43 are inserted and fixed, the through hole part 45 provided so as to penetrate through in a width direction. Also, the engaging part 46 is formed so as to have a width dimension larger than a space dimension between the swelling parts 43, 43. Therefore, the engaging part 46 can be removably engaged and fixed to the engaging member 40, and the attachment and removal part 25 is attachably and detachably formed with respect to the support part 28.

The operation of the endoscope according to the present embodiment is described below.

When the treatment tool insertion part 19 inserted into the endoscope main body part 10 according to the present embodiment is used, with the attachment and removal part 25 being fixed to the support part 28 fixed to an upper part of the tube part 21 in a diameter direction, a treatment tool such as forceps, a snare, or a brush is inserted in the insertion tube 23.

The inserted forceps or the like passes through the tube path 20 in the tube part 21 and is inserted into the treatment tool insertion tube via the tapered part 34 and the pipe 33 formed on the support part 28 to which the tip part of the tube part 21 communicates, thereby allowing a treatment to be performed on a subject as appropriate, for example, in a digestive organ.

Then, after use for a predetermined number of times and when the inside of the tube part 20 is smudged because blood collected from the inside of the digestive organ is suctioned or a lesion is extracted, the attachment and removal part 25 is extracted along the insertion part 26 and removed from the support part 28 while the engagement between the engaging part 46 and the engaging member 40 is being released.

In this case, the engaging part 46 is fixed by the swelling parts 43, 43 in the side piece parts 41, 41 configuring the engaging member 40 and, when the engaging part 46 is extracted, the side piece parts 41 and 41 are warped outward to cause the engaging part 46 to be released. As a result, the insertion tube 23 with the inside of the tube path 20 smudged due to blood collected from the inside of a digestive organ, a lesion, and others is removed from the tube part 21, the attachment and removal part 25 can be cleaned and also subjected to sterilization and disinfection by an appropriate method.

After cleaning and sterilization and disinfection, when the attachment and removal part 25 is again inserted into the tube part 21, the tip part of the insertion tube 23 is inserted into the inside of the insertion part 26 of the support part 28 exposed to the opening 35 formed on the upper part of the tube part 21, and also the engaging part 46 is pressed to fit into the side piece parts 41 and 41 configuring the engaging member 40 via the swelling parts 43, 43.

In this case, the side piece parts 41 and 41 warp outward to receive the engaging part 46, and the swelling parts 43, 43 are placed in the through hole part 45 of the engaging part 46, thereby causing the engaging member 40 to be engaged with the engaging part 46 and causing the attachment and removal part 25 to be fixed in the tube part 21.

Therefore, in the endoscope main body part 10 according to the present embodiment, the attachment and removal part 25 including the insertion tube 23 into which forceps or the like is inserted of the treatment tool insertion part 19 is attachably and detachably provided. With this, as required, the attachment and removal part 25 can be easily removed from the tube part 21 and quickly and easily subjected to cleaning and sterilization and disinfection.

Also, in the present embodiment, the attachment and removal part 25 is made of hard rubber, and its specific structure is simple. Therefore, the manufacturing cost of the attachment and removal part 25 can be reduced, and the attachment and removal part 25 can be made disposable.

Therefore, when the attachment and removal part 25 is used in a disposable manner, even if the attachment and removal part 25 is smudged, cleaning and sterilization and disinfection works are not required, and an endoscope having a cleaner treatment tool insertion part can be provided.

Note that an example has been described in the present embodiment as follows. The engaging member 40 is made of a metal-made leaf spring member formed in an approximately U shape in a longitudinal sectional view, and has the paired side piece parts 41, 41 facing each other and the fixing piece part 42 continuously provided between the paired side piece parts 41, 41. On the paired side piece parts 42, 42, swelling parts 43, 43 formed to project inward are formed. The body 24 has the insertion hollow part 44 for the engaging member 40 formed therein, and the tube part 21 is provided with the engaging part 46 formed of a projection part and having a through hole part 45 where the swelling parts 43, 43 are inserted and fixed. However, the fixing structure is not restricted to the present embodiment.

For example, in the present embodiment, the structure may be such that hole parts capable of communicating to the through hole part 45 are provided to open at portions corresponding to the swelling parts 43, 43, formed on the side piece parts 41 of the engaging member 40 and, with a shaft part to be arranged to penetrate through the through hole part and the hole parts being inserted, the engaging member on a support part side and the engaging part on an attachment and removal part side can be releasably connected to each other. Also, individual components in the present embodiment are not restricted to those in the present embodiment.

INDUSTRIAL APPLICABILITY

The present invention can be widely applied to endoscopic operation device, and therefore has industrial applicability.

DESCRIPTION OF REFERENCE NUMERALS 10 endoscope main body part
11 body
12 joint part
13 endoscope operating device
14 light guide cable
15 air supply/water supply valve
16 upper-and-lower-direction rotation operating part
17 left-and-right-direction rotation operating part
18 operating part
19 treatment tool insertion part
20 tube path
21 tube part
22 cylindrical panel part
23 insertion tube
24 body
25 attachment and removal part
26 insertion part
27 tube path part
28 support part
29 fixing plate part
30 connecting part
31 screw
32 pipe
33 pipe
34 tapered part
35 opening
36 opening
37 thick part
38 sealing member
40 engaging member
41 side piece part
42 fixing piece part
43 swelling part
44 insertion hollow part
45 through hole part
46 engaging part
47 screw
48 O ring
200 endoscope
201 main body part
202 curved part
203 flexible tube
204 operating part 205 rotation dial
206 forceps channel
207 treatment tool insertion part

The invention claimed is:

1. An endoscope comprising:

a flexible tube having a curved part at a tip;

an endoscope main body part for operating a curving operation on the curved part for work; and a treatment tool insertion part, for inserting a treatment tool, projecting from the endoscope main body part and for use in a treatment of a subject by a treatment tool insertion tube arranged in the curved part along an axial direction, wherein the treatment tool insertion part includes:

an attachment and removal part having an insertion tube and a body, the insertion tube having one end inserted in the endoscope main body part to be arranged to communicate to the treatment tool insertion tube and another end placed outside the endoscope main body part, and the body holding and fixing the insertion tube to the endoscope main body part;

a support part provided on the endoscope main body part and having an insertion part and a tube path part, the insertion part through which the insertion tube is inserted and removed, and the tube path part communicating to the treatment tool insertion tube; and an engaging member configured to engage with the body of the attachment and removal part and the support part, and formed of a leaf spring member formed in an approximate U shape, in a cross-sectional view, at a closed end and comprising paired side piece parts, at an open end, facing each other, each having a swelling part thereon projecting inward toward an opposite side piece part, the swelling part being a curve in the leaf spring member.

2. The endoscope according to claim 1, wherein the support part is provided with the engaging member arranged to project from an outer side surface part of the endoscope main body part, and an engaging part can be engaged with the engaging member formed on the endoscope main body part.

3. The endoscope according to claim 2, wherein the engaging member has a fixing piece part continuously provided between the paired side piece parts, the swelling part formed to swell inward, the body has an insertion hollow part of the engaging member formed thereon, and the tube part is provided with an engaging part having a recessed part where the swelling part is inserted and fixed.

4. The endoscope according to claim 2, wherein the support part configures the endoscope main body part and is fixed inside a tube part having an opening on an upper part, with an upper surface part of the support part being provided so as to be exposed from the opening toward outside.

5. The endoscope according to claim 1, wherein the insertion tube is arranged along the axial direction of the endoscope main boy part and diagonally with respect to the axial direction, the body is formed of a covering part covering the insertion tube and a fixing part continuously provided to the covering part and capable of being fixed to a mount part.

6. The endoscope according to claim 2, wherein a mount part is configured as a projection part having an insertion hole, the mount part is provided with an opening that can communicate to the insertion hole and, when the insertion hole and the opening communicate to each other, fixing is made with an insertion member capable of being inserted.

* * * * *